(12) United States Patent
Navab (10) Patent No.: US 10,639,017 B2
(45) Date of Patent: May 5, 2020

(54) TRACKING SYSTEM AND METHOD (71) Applicant: Nassir Navab, Munich (DE)

(72) Inventor: Nassir Navab, Munich (DE)

( * ) Notice: Subject to any disclaimer, the term of this patent is extended or adjusted under 35 U.S.C. 154(b) by 212 days.

(21) Appl. No.: 14/359,644

(22) PCT Filed: Nov. 21, 2012

(86) PCT No.: PCT/EP2012/073269
§ 371 (c)(1),
(2) Date: May 21, 2014

(87) PCT Pub. No.: WO2013/076163
PCT Pub. Date: May 30, 2013

(65) Prior Publication Data
US 2014/0330114 A1 Nov. 6, 2014

(30) Foreign Application Priority Data

Nov. 21, 2011 (EP) ..................................... 11189980

(51) Int. Cl.
*A61B 5/06* (2006.01)
*A61B 17/00* (2006.01)
(Continued)

(52) U.S. Cl.
CPC ........ *A61B 17/00234* (2013.01); *A61B 1/041* (2013.01); *A61B 5/0507* (2013.01);
(Continued)

(58) Field of Classification Search
CPC .............. A61B 17/00234; A61B 1/041; A61B 2017/003; A61B 2034/2057; A61B 2034/301; A61B 2560/0223; A61B 34/20; A61B 34/30; A61B 5/0507; A61B 5/061; A61B 5/062; A61B 5/7405; A61B 5/742; A61B 5/7455; A61B 6/032; A61B 6/037; A61B 8/0841; G01B 11/002; G01B 15/00; G01B 17/00; G01B 21/04; G01B 5/004; G01B 7/003; G01D 5/125; G01S 5/02; G01S 5/18
See application file for complete search history.

(56) References Cited

U.S. PATENT DOCUMENTS 6,288,785 B1 9/2001 Frantz et al.
7,657,302 B2 * 2/2010 Mate .................... A61N 5/1049
128/899

(Continued)

*Primary Examiner* — Michael T Rozanski
(74) *Attorney, Agent, or Firm* — Patterson + Sheridan, LLP (57) ABSTRACT

A system for tracking a tracking element inside a body is provided. It includes a first tracking system, which includes a first tracking sensor for detecting the current position of a tracking element inside a body relative to a nominal position with respect to the first tracking sensor, and a second tracking system, which includes a second tracking sensor for determining the position of the first tracking sensor of the first tracking system relative to the second tracking sensor, and a control unit. The first tracking sensor is movable, and the control unit is configured to deliver a correction signal indicating a deviation of the current position of the tracking element relative to a nominal position with reference to the first tracking sensor. Further, a respective tracking method is provided.

16 Claims, 4 Drawing Sheets

(51) Int. Cl.
  *A61B 8/08* (2006.01)
  *A61B 5/05* (2006.01)
  *A61B 5/00* (2006.01)
  *A61B 6/03* (2006.01)
  *A61B 1/04* (2006.01)
  *G01B 11/00* (2006.01)
  *G01B 15/00* (2006.01)
  *G01B 7/00* (2006.01)
  *G01B 21/04* (2006.01)
  *G01B 17/00* (2006.01)
  *G01B 5/004* (2006.01)
  *G01D 5/12* (2006.01)
  *A61B 34/20* (2016.01)
  *A61B 34/30* (2016.01)
  *G01B 5/18* (2006.01)
  *G01B 5/02* (2006.01)

(52) U.S. Cl.
  CPC .............. *A61B 5/061* (2013.01); *A61B 5/062* (2013.01); *A61B 5/742* (2013.01); *A61B 5/7405* (2013.01); *A61B 5/7455* (2013.01); *A61B 6/032* (2013.01); *A61B 6/037* (2013.01); *A61B 8/0841* (2013.01); *A61B 34/20* (2016.02); *A61B 34/30* (2016.02); *G01B 5/004* (2013.01); *G01B 7/003* (2013.01); *G01B 11/002* (2013.01); *G01B 15/00* (2013.01); *G01B 17/00* (2013.01); *G01B 21/04* (2013.01); *G01D 5/125* (2013.01); *A61B 2017/003* (2013.01); *A61B 2034/2057* (2016.02); *A61B 2034/301* (2016.02); *A61B 2560/0223* (2013.01); *G01B 5/02* (2013.01); *G01B 5/18* (2013.01)

(56) References Cited

U.S. PATENT DOCUMENTS

| | | | |
|---|---|---|---|
| 8,239,002 B2* | 8/2012 | Neustadter | A61N 5/1049 600/424 |
| 9,161,817 B2* | 10/2015 | Olson | A61B 19/2203 |
| 2003/0097061 A1 | 5/2003 | Ferre et al. | |
| 2006/0247520 A1* | 11/2006 | McGee | A61B 6/12 600/434 |
| 2007/0002038 A1 | 1/2007 | Suzuki et al. | |
| 2007/0221233 A1 | 9/2007 | Kawano et al. | |
| 2008/0079421 A1 | 4/2008 | Jensen | |
| 2012/0289821 A1* | 11/2012 | Graumann | A61B 6/08 600/424 |
| 2012/0323111 A1* | 12/2012 | Jain | G06F 19/3437 600/411 |
| 2013/0072787 A1* | 3/2013 | Wallace | A61B 6/12 600/424 |

* cited by examiner

TRACKING SYSTEM AND METHOD

TECHNICAL FIELD

The present disclosure relates to tracking systems. More particularly, it relates to a system and method for tracking one or more elements inside a body, in particular in a human body, for medical purposes.

BACKGROUND OF THE INVENTION

Tracking, i.e. the real-time determination of the spatial relation between objects, is employed in various fields. These include augmented reality, where virtual objects need to be precisely placed with respect to real objects; or navigation, where guidance can be provided between the current and desired location of instruments, or where regions of desired movement may be monitored. For automatic serving of, e.g., camera systems, the location of the moving region of interest may be tracked as well.

In medical applications, a growing field of interest concerns the tracking of the position of objects of various kinds in a human body. These objects to be tracked may, e.g., include devices like cameras, catheters, ultrasound probes, etc., or instruments and tools for the application of substances like medicine or radioactive markers, or surgical instruments for minimally invasive surgery. Currently, there are many different tracking technologies. However, most of them are not suitable for tracking sensors moving within anatomy with no direct access or line of sight, i.e. sensors that are not visible from outside the patient and which are not reachable by a manipulator arm, such as a flexible endoscope or catheter used in various diagnostics or treatment procedures.

U.S. Pat. No. 6,288,785 B1 discloses a system for determining spatial position and/or orientation of one or more objects, the system including an optical subsystem and a non-optical subsystem. US 2007/0225595 A1 discloses a hybrid surgical navigation system for tracking the position of body tissue, including a marker mounted subcutaneously to the tissue and a tracker located above skin level.

A well-known technique for the tracking of devices in a human body is the electromagnetic tracking principle. A typical electromagnetic (EM) tracking system uses a three-axis magnetic dipole source, which is henceforth also called field generator, and a three-axis magnetic sensor, henceforth also called a receiver. From a source excitation pattern of three sequential excitation vectors, each linearly independent of the other two, three sensor output vectors are measured, which contain sufficient information to determine both the position and orientation of the sensor relative to the source, which is equivalent to 6 degrees of freedom (DOF).

Thereby, the electromagnetic field generated by the field generator spreads over a relatively large area, in between the borders of which the receiver can be detected respectively tracked with a certain precision. Generally, the field is not homogeneous, but has gradients, which is typically used in the process of localizing the position of the sensor in the field. Generally, both DC based and AC based systems are used, implying static electromagnetic fields or dynamic electromagnetic fields.

Though in recent years, significant progress has been made in improving the above techniques, there are a number of inherent drawbacks which can hardly, or only with significant effort, be overcome. Mainly, anything in the electromagnetic field which causes the field to be distorted will result in measurement noise and/or errors. For example, ferromagnetic metallic objects cause the field to be distorted, which is particularly relevant in clinical environments.

Further, eddy currents are induced in nearby metals by a changing EM field, which happens throughout each measurement period with AC trackers. DC-based trackers were developed in an attempt to alleviate this problem. The magnetic field produced by ferromagnetic materials affects both AC and DC trackers, and has a frequency dependency which generally diminishes with frequency.

In general, static distortions of the EM field may be determined in a calibration procedure. For example, the distortion may be calculated with respect to some ground truth, e.g. obtained with an alternative tracking system like IR-optical tracking. During operation, this information can then be used to estimate the true position and orientation via different methods. Such a calibration usually can not span the full 6 DOF parameter space, which is due to an exponential increase of data points.

On the other hand, dynamic distortions of the EM field, e.g. due to objects introduced into the field during operation, may be detected with consistency checks between multiple sensors fixed relative to each other. The measured spatial relation between those sensors should be static, and otherwise a distortion of the EM field may be assumed, which is however not a safe conclusion.

To sum up, in contrast to mechanical arms or optical tracking camera systems, known magnetic tracking solutions do not provide the accuracy and stability required by many clinical procedures, while nevertheless, they require significant effort, labor and cost for the correction of errors inherent to the principle, as was described above.

In view of the above, there is a need for a tracking system for tracking elements in a body which overcomes the shortcomings of the known solutions.

SUMMARY OF THE INVENTION

The problems mentioned above are at least partly solved by a system for localizing a tracking element inside a body according to claim 1, and a method for localizing the position of a tracking element inside a body according to claim 8.

In a first aspect, a system for tracking a tracking element inside a body is provided. The system includes a first tracking system, including a first tracking sensor for detecting the current position of a tracking element inside a body relative to a nominal position with respect to the first tracking sensor, and a second tracking system, including a second tracking sensor for determining the position of the first tracking sensor of the first tracking system relative to the second tracking sensor, and a control unit, wherein the first tracking sensor is movable, and wherein the control unit is configured to deliver a correction signal indicating a deviation of the current position of the tracking element relative to a nominal position with reference to the first tracking sensor.

In a second aspect, a method for tracking the position of a tracking element inside a body is provided. It includes positioning a tracking element inside a body; positioning a first tracking sensor in the vicinity of the body, so that the sensor is able to detect the tracking element; determining a first relative position of the tracking element with respect to the first tracking sensor, in a first coordinate system; and maintaining, within a predefined tolerance space, the first relative position between the tracking element and the first tracking sensor, when the tracking element changes its position relative to the body.

Further aspects, advantages and features of the present invention are apparent from the dependent claims, the description and the accompanying drawings.

BRIEF DESCRIPTION OF THE DRAWINGS

A full and enabling disclosure, including the best mode thereof, to one of ordinary skill in the art is set forth more particularly in the remainder of the specification, including reference to the accompanying figures wherein.

DETAILED DESCRIPTION OF THE INVENTION

Reference will now be made in detail to various embodiments, one or more examples of which are illustrated in each figure. Each example is provided by way of explanation and is not meant as a limitation. For example, features illustrated or described as part of one embodiment can be used on or in conjunction with other embodiments to yield yet further embodiments. It is intended that the present disclosure includes such modifications and variations.

Within the following description of the drawings, the same reference numbers refer to the same components. Generally, only the differences with respect to the individual embodiments are described. When several identical items or parts appear in a figure, not all of the parts have reference numerals in order to simplify the appearance.

The systems and methods described herein are not limited to the specific embodiments described, but rather, components of the systems and/or steps of the methods may be utilized independently and separately from other components and/or steps described herein. Rather, the exemplary embodiment can be implemented and used in connection with many other applications, in particular with other medical diagnostic or treatment methods than the ones exemplarily shown.

As used herein, the term "field generator" is used interchangeably with "transmitter". Further, it shall be noted that in the following the field generator is generally assumed to be located outside the body, while the receiver, also called tracking element, is generally located inside the body. However, in embodiments, the receiver and field generator may also be exchanged in position, such that the field generator is inside the body as a tracking element, and the receiver is outside the body, having the function of the first tracking sensor. Hence, the function and location of the first tracking sensor and the tracking element are strictly defined, whereas the role of the field generator (transmitter) and receiver may be exchanged with each other. Further, the term "pose" as used herein is defined as including data about the position of a respective object in space, as well as about an orientation thereof, thus typically including data about 6 degrees of freedom (DOF) or 6 dimensions. Further, the term "position" as used herein is understood to include the properties of a "pose", hence the terms are used interchangeably, unless otherwise stated or unless technically unfeasible.

Embodiments described herein use the magnetic tracking functionality to detect a target/tracking element, and to position the portable field generator and the receiver at a given well pre-calibrated relative pose, or within a small distance such that the precision of the magnetic positioning is high. Once this is done, the external coordinates of the field generator are tracked and estimated using a secondary sensing system, e.g. optical or mechanical tracking systems, which is responsible also for tracking the field generator and indirectly the deep seated target. In fact, the final position of the target (receiver) is estimated through the composition of the two transformations: a) the position in regard to the field generator (with little variation), and b) the position of the portable field generator, which is moving throughout the space to keep relatively fixed distance to the receiver and is tracked by another external tracking system, e.g. optical or mechanical tracking systems, with high accuracy and stability.

Hence, a portable/movable field generator is used, which is itself localized with another sensing technology, e.g. (non-limiting) with an optical tracking system, a mechanical arm or the like. The portable field generator and the receiver inside the patient form a magnetic localization system. During operation, the field generator is moved in order to keep the receiver at a given distance or within a particular predefined space with respect to the generator, for which the detection is optimal and for which a pre-calibration has been done.

In other words, the movable field generator is moved in order to keep the receiver inside the body at basically the same nominal position with respect to the field generator, when the position of the receiver in the body respectively patient changes. Thus, the position of the field generator is kind of following the position of the moving receiver in the body, in order to maintain their spatial relationship with respect to each other. In a technical realization, it is typically tried to keep the receiver within a certain tolerance space around the defined nominal position, which is, e.g., defined by a tolerance in every spatial direction, resulting in a sphere around the exact nominal position with respect to the field generator. By doing so, the position of the receiver with respect to the field generator is kept constant (defined as being within the tolerance space), and the system works always at an optimal predefined operating point. While the position of the field generator is tracked by a further tracking system, the position and orientation (together forming the pose) of the receiver inside the body is known with respect to the field generator, so that in effect the position of the receiver may be calculated with respect to, as an example, the examination room. Knowing also the position of the patient's body with respect to the room by means of a further observation system, the receiver may then be visualized together with, e.g., 3D pictures of the patient.

Thereby, the movement of the field generator may be carried out in a variety of ways. In a simple realization, the field generator is mounted to a mechanical arm without actuators. The arm is designed such that the field generator is stably held, but may manually be moved by a user. When the receiver in the patient moves, the tracking system signalizes the direction of movement to the user, so that the user can move the field generator at the arm to a new position, thus maintaining the spatial relationship between field generator and receiver as described above. The signalization can of course be carried out in a huge variety of ways, e.g. (non-limiting) by display of numbers or symbols on a display, by an acoustical device, by haptic feedback through a special glove, by a semi-transparent goggle with LCD elements, or any combination of the further. The field generator may also be mounted to a movable slide below a laying surface of a bed on which the patient is resting. That is, the field generator is positioned movable below the patient, more precisely below a laying surface, e.g. in a space provided in the patient bed, or entirely under the bed. This may be realized by a system with a slide which is moved by a wire or belt in one dimension, whereby the belt together with its drive is moved in a second (perpendicular) dimension on, e.g., at least one rail. The materials of the bed have to be chosen in order to not interfere with the electromagnetic tracking system.

Thereby, the position of the field generator may be determined/tracked by position sensors on the mechanical arm, by an optical tracking system supervising tracking markers on the arm and/or field generator, or the like.

In embodiments, the tracking system has a control unit. This unit may also be used to process the information about the moving receiver in order to move the field generator via any type of actuators. In the example above, the actuators may move the mechanical arm, hence implementing a robot arm automatically following the receiver with the field generator.

Figure 1:
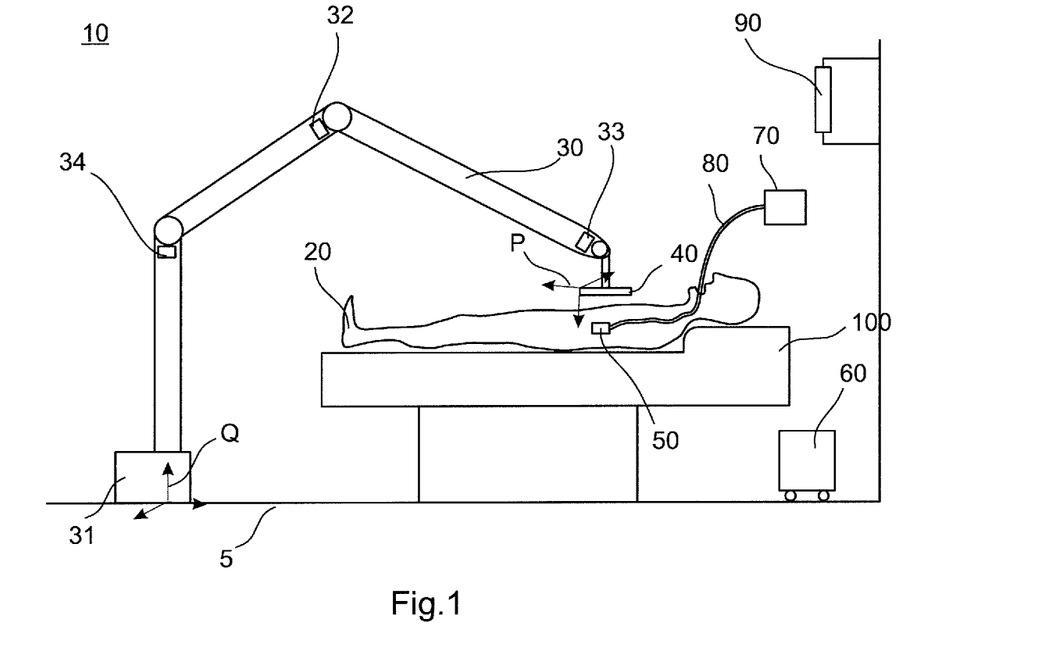
FIG. 1 schematically shows a perspective view of a tracking system according to embodiments.

FIG. 1 shows a tracking system 10 according to embodiments. The first tracking sensor 40, which is typically, but not necessarily a field generator, is mounted to a mechanical arm 30. The arm 30 may be configured to be manually movable by an operator. In the figure, tracking element 50 is mounted at the end of a tube 80, which may for example be part of a camera system with a camera 70. The camera may e.g. be an optical camera, an ultrasound device, or a PET/SPECT device or nuclear imaging device. As was laid out, the tracking element 50 is typically a magnetic receiver having a three axis geometry. The receiver is connected via cables (not shown) through tube 80 with a control unit 60, which is also connected to the first tracking sensor 40 (all connections may generally be wireless or wired and are not shown).

The mechanical arm 30 is equipped with a plurality of position sensors 32, 33, 34 connected to the control unit, such that a 3D position of the first tracking sensor 40 may be determined. When the position of the base 31 of the arm 30 in the room 5 is known, the exact position of the tracking sensor 40 in the room 5 can be calculated by the control unit 60. Hence, the whole arm 30 is regarded as a tracking sensor in this case, wherein the pose of the first tracking sensor 40 is typically determined in a coordinate system Q having a defined position with respect to the mechanical arm 30. When also the spatial relationship between the body 20 and the base 31 is known, the exact position of the tracking sensor 40 with respect to the body 20 can be calculated. As was laid out, the position (or pose) of the tracking element 50 inside the body relative to the tracking sensor 40 is well defined and maintained during tracking, such that in effect the position of the tracking element 50 inside the body 20 may be calculated and displayed. It is understood that the coordinate system Q may also be positioned at another position than shown in FIG. 1, and that it may suitably be chosen as a cartesian, cylindrical, spherical, or other type of coordinate system, which are merely questions of technical realization.

In order to use the described system, the following steps may be carried out. When the patient lays down on table 100, the tracking element 50 is inserted into the body 20, for example as it is fixed to the end of a tube 80 belonging to a camera system with a camera 70. As the tracking element is fixed to the end of the tube 80 bearing also the ocular of the camera, it may be tracked where the viewpoint of the camera is and in which direction it is viewing. Once the camera tube 80 being attached to the tracking element is inserted into the patient's body, the first tracking sensor 40 is positioned in the vicinity of the body, so that the sensor is able to detect the tracking element 50. This typically means that the sensor is positioned close to the body surface of the patient, in an area close to the position where the end of the tube 80 with the tracking element is assumed.

Then, the position of the tracking element 50 with respect to the first tracking sensor 40 is determined. The control unit 60 is configured to display the deviation of the relative position of the tracking element 50 from a nominal position with respect to the first tracking sensor 40, wherein the nominal position is typically defined as a predefined position allowing an optimal, or at least very good, working point of the sensor. The control unit is configured to display to a user the deviation, such that the user may move the first tracking sensor 40 manually until the nominal relative position of the tracking element 50 has been reached, so that a displayed deviation is minimized or vanishes.

The displaying is carried out by a unit 90, which may display the deviation on a conventional screen, or by acoustic signalling, by artificial or pre-recorded voice, or using tactile means such as a glove having feedback elements. When the position of the tracking element 50 inside the body changes, e.g. when it is manually moved further into the body 20, the unit 90 displays the resulting deviation of the position of the tracking sensor from its nominal position with respect to the tracking sensor to the user/operator. The user then moves first tracking sensor 40 into the direction indicated by the unit 90. The sensors 32, 33, 34 on arm 30 register the change of position (or pose) of the tracking sensor 40, which information is used by the control unit 60 to update the calculated position of the tracking element.

The change of position may then be displayed together/overlayed with, as example, live images or pre-operative images of the body 20 acquired by a further imaging system, e.g. X-ray computer tomography images, nuclear magnetic resonance images or images acquired by nuclear imaging. This optical display may also be integrated in unit 90.

The control unit typically calculates the position of the tracking element 50 with respect to the first tracking sensor 40 in a first coordinate system P, which has its center at the first tracking sensor, and also moves together with the first sensor. On the other hand, the position of the first tracking sensor 40 is calculated in relation to a second coordinate system Q, which is typically fixed at the second tracking sensor, hence the mechanical arm 30 in FIG. 1 or the optical tracking sensor 110 in FIG. 2. It is obvious for a skilled person, that the coordinate systems may be chosen differently, and that the described scenario is just one non-limiting example of many possible ways of implementing a calculation of the spatial relationships between the different parts involved.

Figure 2:
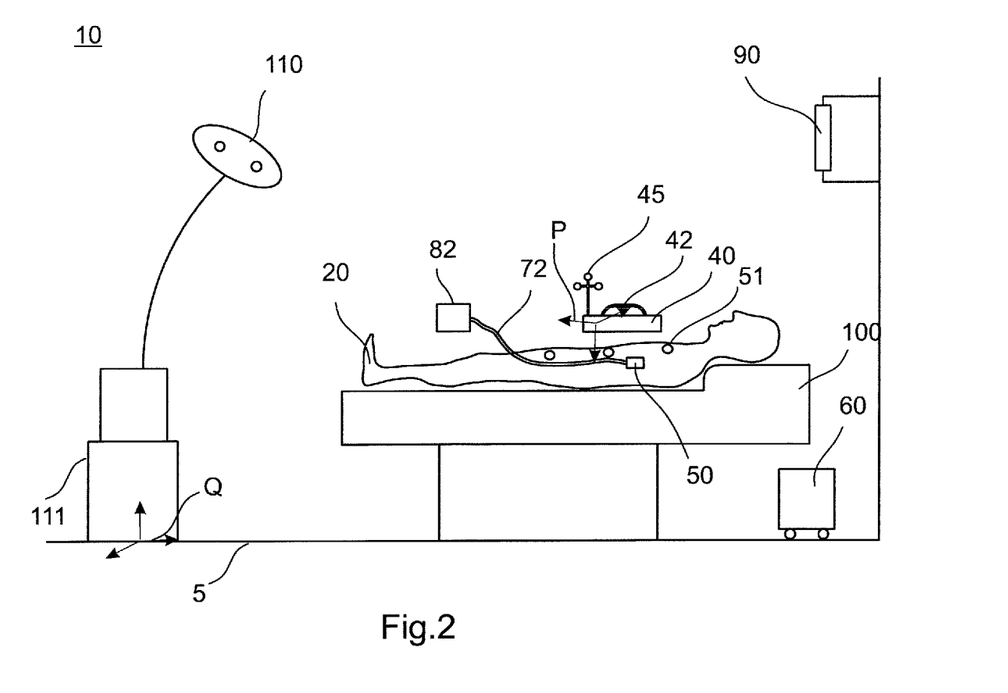
FIG. 2 schematically shows a perspective view of a further tracking system according to embodiments.

FIG. 2 shows a tracking system according to embodiments, showing a case where the end of a catheter 72, connected to, e.g., an external camera 82, is equipped with tracking element 50. Instead of the arm of FIG. 1, an optical sensor 110 of a second tracking system is used to monitor the position of the first tracking sensor 40. For this purpose, one or more optical markers 45 are attached to sensor 40. The optical sensor 110 can also be used to acquire the data about the exact position of the body 20 with respect to the sensor 110. To this end, markers 51 may be attached to the body. As both the data about the position of the first tracking sensor 40 and the position data of the body 20 is acquired with respect to the position of, and by, sensor 110, the control unit 60 may directly correlate the calculated position of the tracking element 50 with the position data for the body 20. The first tracking sensor 40 has a handle 42 with which it can be held by an operator. The operator may not need to hold the sensor 40 in place all the time during an examination, but can put the sensor occasionally aside, for example in phases when the tracking element is not moved from outside. As soon as a change of position of the end of tube 72, 80 is carried out, the operator may take the sensor and put in a position where the tracking element has previously been detected. This may be assisted by the above described displaying and signaling by the control unit 60. Similarly to FIG. 1, also an adjustable mechanical arm 30 may be employed to hold the sensor 40 in place.

Figure 3:
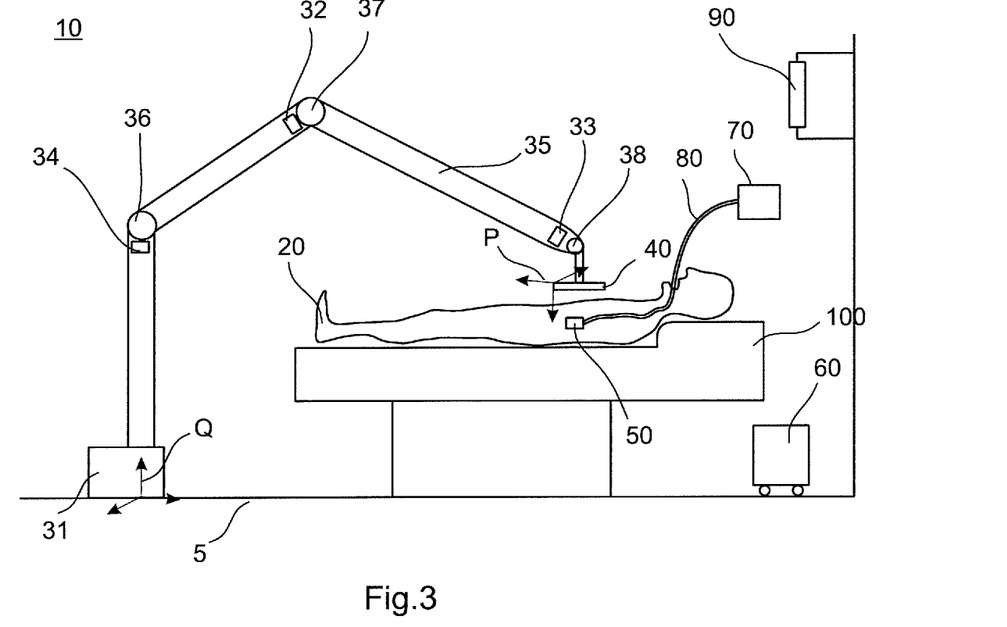
FIG. 3 schematically shows a perspective view of a yet further tracking system according to embodiments.

FIG. 3 shows a tracking system according to embodiments. Therein, calculated feedback from the control unit 60 about the position deviation of the tracking element 50 with respect to the first tracking sensor 40, which may be displayed to a user as described above, is used to automatically alter the position of the first tracking sensor 40. That is, the correction signal indicating a deviation of the current position of the tracking element 50 relative to the nominal position with reference to the first tracking sensor 40 is used to control an actuator which changes the position of the first tracking sensor, as a reaction to the tracking element 50 changing its position inside the body. The actuator may be realized by a mechanical arm as in FIG. 1, which is additionally equipped with devices such as electro motors 36, 37, 38, such that it is effectively a robotic arm 35 controlled by the control unit 60. The robotic arm 35 is moved via actuators 36, 37, 38 by the control unit 60 in such a way that the relative position of the tracking element 50 with respect to the tracking sensor 40 is maintained within a predefined tolerance space, which may for example be a sphere with a radius of 0.3 to 2 mm.

In embodiments, the tracking sensor 40 may also be from a different type than a magnetic sensor, as non-limiting examples, a detector for radioactive radiation, for ultrasound, or for radio frequency such as terahertz waves. It could, as non-limiting examples, be a PET sensor, a SPECT sensor, or a gamma camera. In the latter cases, the tracking element 50 is configured to emit a radiation which may be detected by the first tracking sensor.

In embodiments, the determination of the position and shape of the body (20) may be carried out not by means of the optical sensor 110, but by a further, independent imaging or tracking system. In this case, typically the position is determined with respect to a further, third coordinate system (not shown), the position data of which has to be correlated by the control unit 60 with the data acquired with respect to the first and second coordinate systems P and Q (cf. FIG. 1, FIG. 2 and FIG. 3).

Figure 4:
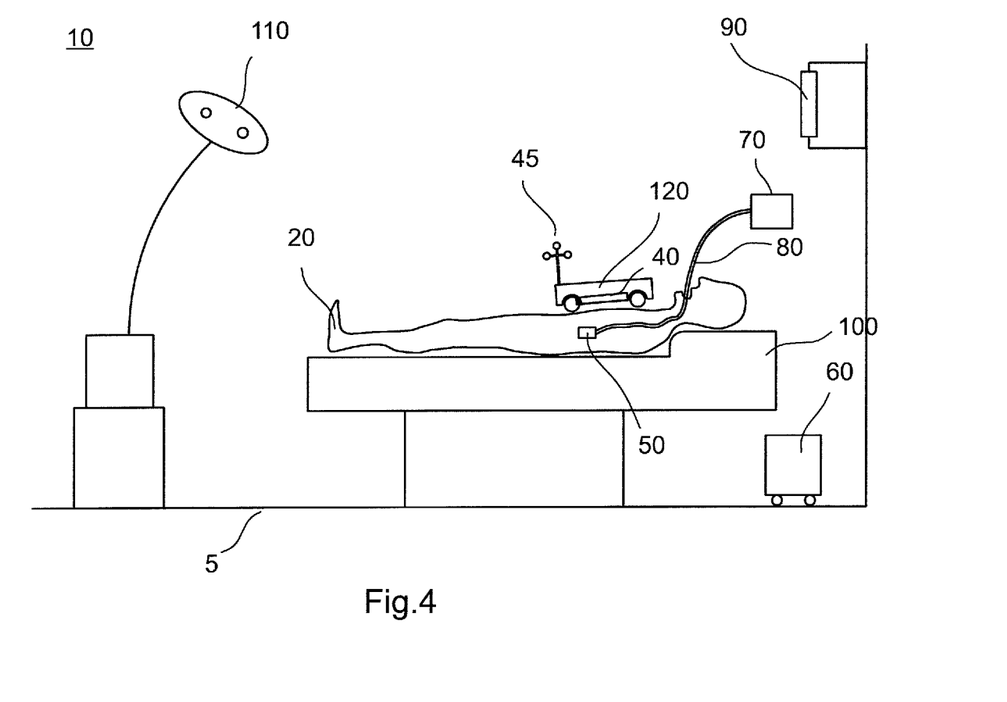
FIG. 4 schematically shows a perspective view of a further tracking system according to embodiments.

FIG. 4 shows a tracking system according to embodiments, wherein the first tracking sensor 40 is connected to a self-driven robotic device 120, which is controlled by the control unit 60. When the tracking element 50 moves inside the body 20, the deviation from the nominal position with respect to the sensor 40 is detected as described before. However, the deviation of the tracking element's position from its nominal position is processed by the control unit into a control/steering signal for the robotic device 120, so that the device changes its position by motorized action of its wheels, until the tracking element 50 is again at its nominal position, or at least within a tolerance level in its vicinity. In this configuration, no adjustment of the height of the sensor 40 is possible due to the limitations to the robot's mobility. Hence, the control unit may be configured to just take into account deviations in the horizontal plane, hence two dimensional, while in the other cases described above, the position is usually in three dimensions. However, also with a robotic device/vehicle 120, the sensor may be moved in a third dimension, respectively a z-axis or height axis with respect to the patient. For this purpose, the sensor 40 is, for example, moved by an actuator built into the robotic device, in a direction of a height axis of the device, which can allow a height movement of the sensor 40 of up to, e.g., 10 to 15 cm.

Additionally, the control unit 60 may calculate the timely deviation of the position change of the tracking element 50, hence its speed, and may send this information to the vehicle or another one of the actuators described before, which may be used for improving the reaction time for the correctional movement of tracking sensor 40.

Figure 5:
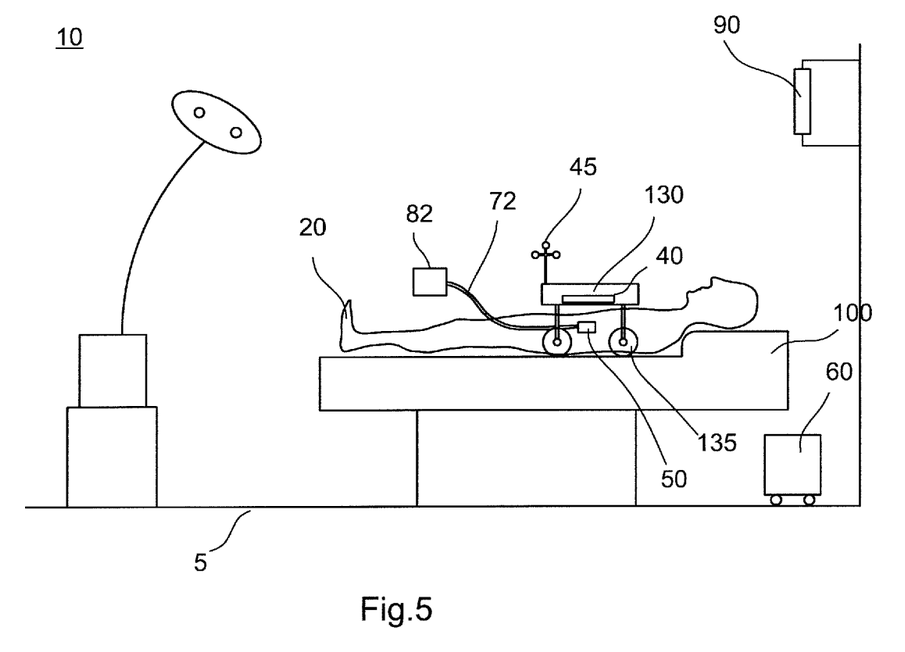
FIG. 5 schematically shows a perspective view of a yet further tracking system according to embodiments.

FIG. 5 shows a tracking system according to embodiments, which is basically a modification of the system shown in FIG. 4. The wheels/chains of robotic vehicle 130 in this case have contact to the table 100, so that the mobility in a direction lengthwise to the body 20 is higher than in FIG. 4. In the direction perpendicular to the paper plane, a movement of the tracking sensor 40 may be enabled by a separate actuator (not shown). In this manner, the sensor 40 may cover the biggest part of the upper part of the body 20. As in FIG. 3, the position of the tracking sensor 40 is tracked by the optical sensor 110 via the optical marker 45 attached to the sensor, such as in FIG. 2 and FIG. 3.

Figure 6:
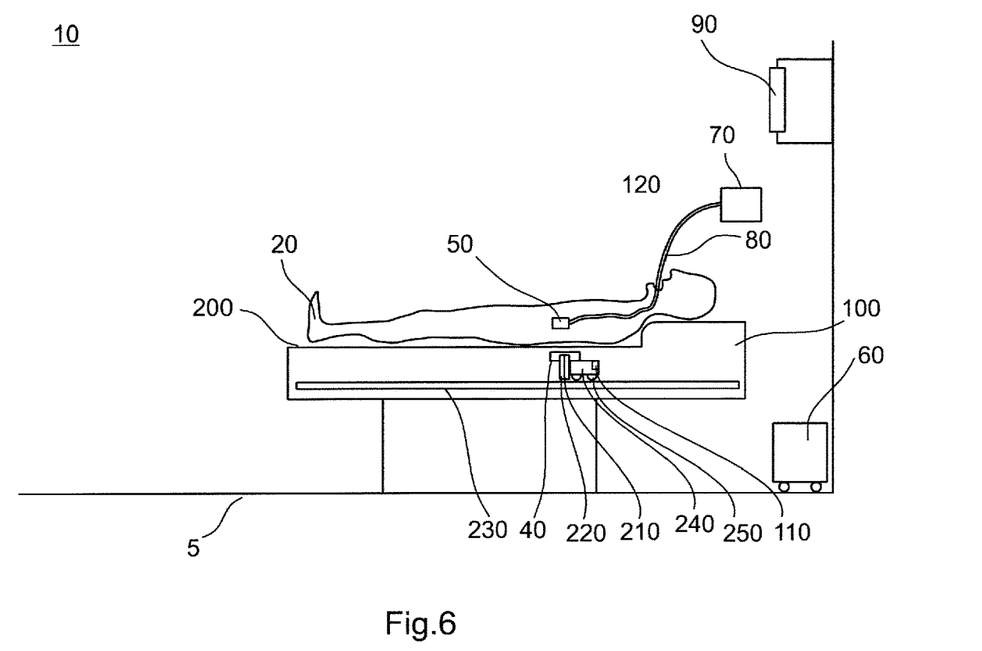
FIG. 6 schematically shows a perspective view of a further tracking system according to embodiments.

FIG. 6 shows a tracking system 10 according to embodiments. The first tracking sensor 40, which is typically, but not necessarily a field generator, is thereby moved by a wire or belt 210 in a first dimension/direction defined by the belt (perpendicular to the drawing plane in FIG. 6). The belt 210 is driven via a roller 220 by at least one actuator 240. The actuator 240 is also movable by an integrated motor via rollers 250 on one or two rails 230. At least one tracking sensor 110, which may e.g. be positioned at the actuator 240, delivers data about the position of the first tracking sensor 40 with respect to a reference coordinate system, which may e.g. be defined in relation to the bed 100. Thereby, the elements described are positioned below a laying surface 200 of the bed 100, e.g., in a space provided in the mattress of the bed, or in a hollow space of the bed 100 designed to host the above mechanism. It is understood that the movability of the sensor 40 below the laying surface 200 can be achieved in a multitude of ways, i.e. different mechanical configurations, which are also regarded to fall into the scope of the present application. Further, there may be an arrangement of a plurality of sensors 40 below the patient, which can be arranged to be movable about an area covering only a fraction of the laying surface 200, such that the whole laying surface, or significant part of it, is covered as a superposition from the various sensors. The above configuration allows the tracking as in other embodiments, but with a much more compact appearance, which is also space saving and leaves more room for medical personnel around the bed 100.

Figure 7:
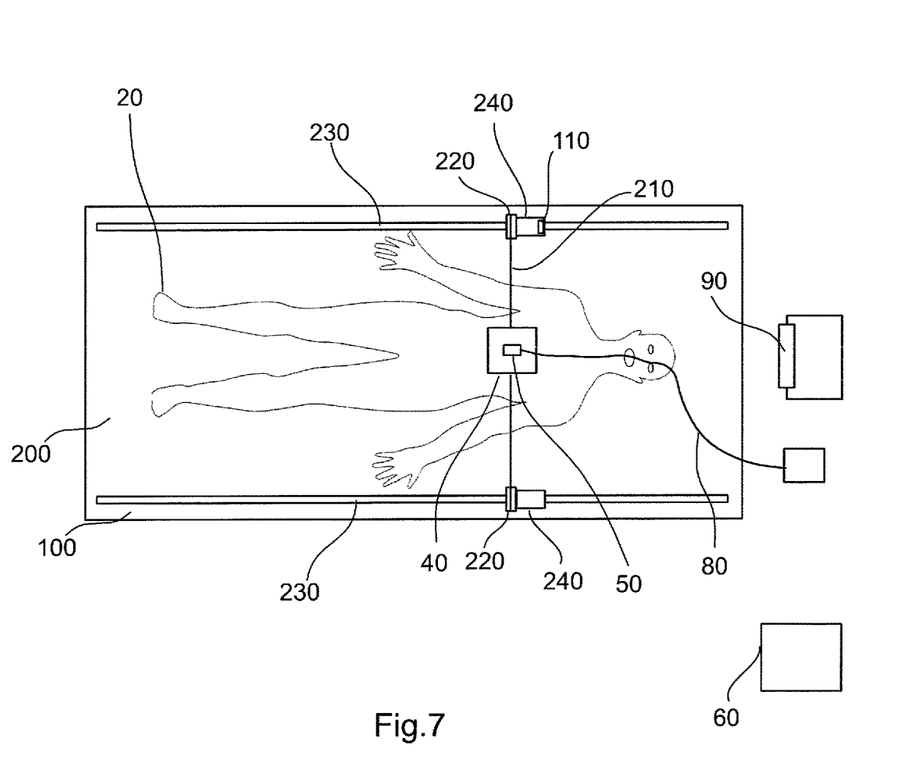
FIG. 7 schematically shows a perspective top view of the tracking system of FIG. 6.

FIG. 7 shows a top view of the embodiments of FIG. 6. Thereby, elements 210, 220, 230, and 240 below the laying surface 200 of the bed are drawn with solid lines for illustrational purposes, whereas they would not be visible from this perspective, such as the tracking element 50 inside the patient and the part of catheter 80 from the mouth to the element 50.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. While various specific embodiments have been disclosed in the foregoing, those skilled in the art will recognize that the spirit and scope of the claims allows for equally effective modifications. Especially, mutually non-exclusive features of the embodiments described above may be combined with each other. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system for tracking a tracking element inside a body, comprising:
    a first tracking system, the first tracking system comprising:
        a first non-contact tracking sensor comprising a magnetic sensor for detecting a current position of a tracking element inside a body relative to a position of the first non-contact tracking sensor while the first non-contact tracking sensor is spaced from and outside the body;
    a second tracking system configured to determine the position of the first non-contact tracking sensor, the second tracking system comprising:
        a second tracking sensor in signal communication with the first non-contact tracking sensor configured to detect the position of the first non-contact tracking sensor of the first tracking system relative to the second tracking sensor; and
    a control unit connected to the first non-contact tracking sensor and the second tracking sensor,
    wherein the first non-contact tracking sensor is provided to be movable with respect to the body,
    wherein the current position of the tracking element detected by the first non-contact tracking sensor is a first position in a first coordinate system,
    wherein the first coordinate system moves together with the first non-contact tracking sensor,
    wherein the position of the first non-contact tracking sensor detected by the second tracking sensor is a second position in a second coordinate system,
    wherein the second coordinate system is associated with the second tracking sensor, and
    wherein the control unit is configured to:
        calculate a position of the tracking element with respect to the second tracking sensor by composing the detected current position of the tracking element relative to the first non-contact tracking sensor with the detected position of the first non-contact tracking sensor in the first coordinate system relative to the second tracking sensor in the second coordinate system; and
        deliver a correction signal to move the first non-contact tracking sensor if the detected current position of the tracking element relative to the first non-contact tracking sensor deviates from a substantially constant target position of the tracking element relative to the first non-contact tracking sensor, wherein the substantially constant target position is within a tolerance space around a pre-calibrated relative position of the tracking element and the first non-contact tracking sensor.

2. The system of claim 1, further comprising:
    an optic, acoustic, or haptic display coupled to the control unit and configured to provide a display of the correction signal to a user.

3. The system of claim 1, further comprising:
    at least one actuator controlled by the control unit to move the first non-contact tracking sensor in response to a change in position of the tracking element, wherein the at least one actuator is configured to move the first non-contact tracking sensor in response to the correction signal, so that the relative position of the tracking element with respect to the first non-contact tracking sensor is maintained within the tolerance space.

4. The system according to claim 1, wherein the second tracking system comprises at least one of: a mechanical arm, a robot arm, an optical tracking sensor, a radio frequency based tracking system, or a robotic vehicle.

5. The system according to claim 1, further comprising a patient bed with a laying surface for a patient, and wherein the first non-contact tracking sensor is located movable below the laying surface.

6. The system according to claim 5, wherein the first non-contact tracking sensor is movable by at least one belt.

7. The system of claim 1, wherein the tolerance space has a radius of 2 mm or less.

8. A method for tracking a position of a tracking element inside a body, comprising:
    positioning a tracking element inside a body;
    positioning a first non-contact tracking sensor comprising a magnetic sensor in a vicinity of the body and spaced from and outside the body, so that the sensor is able to detect the tracking element, wherein the first non-contact tracking sensor is movable with respect to the body;
    determining a first relative position of the tracking element with respect to the first non-contact tracking sensor in a first coordinate system that moves together with the first non-contact tracking sensor, wherein the first relative position is within a tolerance space around a pre-calibrated relative position of the tracking element and the first non-contact tracking sensor;
    determining a second relative position of the first non-contact tracking sensor with respect to a second tracking sensor in a second coordinate system associated with the second tracking sensor;
    calculating a position of the tracking element with respect to the second tracking sensor by composing the first relative position in the first coordinate system with the second relative position in the second coordinate system; and
    maintaining the first relative position between the tracking element and the first non-contact tracking sensor at a substantially constant target position, when the tracking element changes its position relative to the body by actively moving the first non-contact tracking sensor with respect to the body, wherein the substantially constant target position is within the tolerance space;
wherein maintaining the first relative position comprises moving the first non-contact tracking sensor in response to the tracking element changing to a position outside of the tolerance space.

9. The method of claim 8, wherein maintaining the first relative position comprises:
manually moving the first non-contact tracking sensor in response to a correction signal displayed to a user, or
moving the first non-contact tracking sensor via an actuator controlled by a control unit.

10. The method of claim 9, wherein the actuator moving the first non-contact tracking sensor comprises at least one of: a robot arm, an automated vehicle, a belt, and a rail, both the belt and the rail below a laying surface of a patient bed, which actuator is controlled by the control unit.

11. The method of claim 8, wherein maintaining the first relative position between the first non-contact tracking sensor and the tracking element comprises a deviation of a current position from the first relative position that is minimized, but not zero, if external factors prevent the first relative position from being precisely maintained.

12. The method of claim 8, wherein a deviation signal carries information about a deviation in two spatial dimensions (x, y) or in three spatial dimensions (x, y, z), and information about a rate of change per time unit.

13. The method of claim 8, wherein a position of the body is determined in at least one of the first coordinate system and the second coordinate system by tracking markers attached to the body.

14. The method of claim 13, wherein the position of the body is detected by an optical tracking system, which tracks the markers on the body, in a third coordinate system.

15. The method of claim 14, further comprising:
correlating the position of the body with the position of the first non-contact tracking sensor,
calculating the position of the tracking element inside the body, and
displaying the position of the tracking element in preoperative or live images of the body acquired by at least one further imaging system comprising at least one of X-ray computed tomography, nuclear magnetic resonance or a nuclear imaging method.

16. The method of claim 8, wherein the tolerance space has a radius of 2 mm or less.

* * * * *